United States Patent [19]

Zaromb

[11] Patent Number: 4,977,095
[45] Date of Patent: * Dec. 11, 1990

[54] LIQUID-ABSORPTION PRECONCENTRATOR SAMPLING INSTRUMENT

[75] Inventor: Solomon Zaromb, Hinsdale, Ill.

[73] Assignee: The United States of America as represented by the United States Department of Energy, Washington, D.C.

[*] Notice: The portion of the term of this patent subsequent to Mar. 27, 2007 has been disclaimed.

[21] Appl. No.: 330,655

[22] Filed: Mar. 30, 1989

Related U.S. Application Data

[63] Continuation-in-part of Ser. No. 892,990, Aug. 4, 1986, Pat. No. 4,829,008.

[51] Int. Cl.$^5$ .............................................. G01N 1/18
[52] U.S. Cl. ................................... 436/178; 436/161; 436/168; 436/169; 436/514; 422/56; 422/69; 422/88; 422/89; 55/16; 55/158; 73/864.81; 73/864.83
[58] Field of Search ............... 436/178, 161, 168, 169, 436/167, 514; 422/69, 56, 88, 89, 220; 55/16, 158; 73/864.81, 864.83

[56] References Cited

U.S. PATENT DOCUMENTS

| | | | |
|---|---|---|---|
| 1,141,266 | 6/1915 | Raschig | 422/220 |
| 2,704,702 | 3/1955 | Pike | 422/220 X |
| 4,235,601 | 11/1980 | Deutsch et al. | 436/514 |
| 4,359,323 | 11/1982 | LePage | 436/161 X |
| 4,407,963 | 10/1983 | Sorensen | 422/88 X |
| 4,529,521 | 7/1985 | Cortes et al. | 436/161 X |
| 4,549,965 | 10/1985 | Davis | 436/161 X |
| 4,808,350 | 2/1989 | Robbins et al. | 261/96 |
| 4,829,008 | 5/1989 | Zaromb | 422/69 X |

Primary Examiner—Robert J. Warden
Assistant Examiner—Lynn M. Kummert
Attorney, Agent, or Firm—Mark P. Dvorscak; Robert J. Fisher; William R. Moser

[57] ABSTRACT

A system for detecting trace concentrations of an analyte in air and includes a preconcentrator for the analyte and an analyte detector. The preconcentrator includes an elongated tubular container in which is disposed a wettable material extending substantially the entire length of the container. One end of the wettable material is continuously wetted with an analyte-sorbing liquid, which flows to the other end of the container. Sample air is flowed through the container in contact with the wetted material for trapping and preconcentrating the traces of analyte in the sorbing liquid, which is then collected at the other end of the container and discharged to the detector. The wetted material may be a wick comprising a bundle of fibers, one end of which is immersed in a reservoir of the analyte-sorbing liquid, or may be a liner disposed on the inner surface of the container, with the sorbing liquid being centrifugally dispersed onto the liner at one end thereof. The container is preferably vertically oriented so that gravity effects the liquid flow.

22 Claims, 1 Drawing Sheet

LIQUID-ABSORPTION PRECONCENTRATOR SAMPLING INSTRUMENT

The U.S. government has rights in this invention pursuant to Contract No. W-31-109-ENG-38 between the U.S. Department of Energy and The University of Chicago representing Argonne National Laboratory.

REFERENCE TO RELATED APPLICATION

This is a continuation-in-part of copending U.S. application Ser. No. 892,990, filed Aug. 4, 1986, entitled "Analytical Instrument with Apparatus and Method for Sample Concentrating" (S-64,128), now U.S. Pat. No. 4,829,008, the disclosure of which is incorporated herein by reference.

BACKGROUND OF THE INVENTION

The present invention relates to analytical instruments for detecting and identifying trace levels of selected vapors, and in particular to portable instruments.

This invention relates to detection and identification of various vapors in gaseous media, such as air. The invention relates to hazardous gas detection, but has particular application to the detection of explosives and other illegal substances in the baggage and cargoes of boats, aircraft, or other vehicles.

The detection of explosives in baggage and other cargo presents a formidable challenge to present detection technologies. The room temperature equilibrium vapor pressures of such explosives as cyclonite (RDX) and pentaerythritol tetranitrate (PETN) are $1.1 \times 10^{-9}$ torr and $3.8 \times 10^{-10}$ torr, which translates to 1.4 ppt (parts per trillion) and 0.5 ppt, respectively, at atmospheric pressure. Another explosive denoted as HMX, has a room temperature equilibrium vapor concentration of about 0.1 ppt at atmospheric pressure. Even the more common explosives, such as nitroglycerin (NG), dinitrotoluene (DNT) and trinitrotoluene (TNT), with the relatively high equilibrium vapor concentrations of 300 ppb (parts per billion), 140 ppb and 6 ppb, respectively, may be expected to give off much lower concentrations, probably in the sub-ppt range, in the space surrounding a well-packaged explosive, especially if the package had been introduced into that space less than an hour earlier. Not only will the vapor get highly diluted as it diffuses into the surrounding space, but also most of that vapor will get lost by adsorption onto the surrounding materials. These dilution and adsorption effects may be expected to bring down the actual concentrations of the low-vapor-pressure explosives, such as RDX, PETN or HMX, down to 1 ppq (part per quadrillion) or less.

It is known to preconcentrate analytes in air samples by the use of sorbents, such as charcoal, Tenax TM, or silica gel, but such techniques have the disadvantage of requiring desorption and sorbent-reconditioning steps, and they also risk possible introduction of interfering contaminants from the sorbents, analyte breakthrough, and the like.

A preconcentrator-sampler has been developed for use with a highly sensitive ion mobility spectrometer, and is based on adsorption of explosive vapors on quartz, followed by their thermal desorption at about 140° C. But the possibility of thermal decomposition of some of the explosives molecules at or near 140° C. is a cause for concern and renders the device unsuitable for the detection of those compounds that tend to decompose at temperatures above 100° C.

Neutron activation has been used to detect the atomic composition of a concealed explosive, but this may be masked by harmless substances of similar atomic composition.

The aforementioned copending U.S. application Ser. No. 892,990 discloses the use of an absorption preconcentrating air sampler to increase the sensitivity of an analytic instrument. In such a sampler, a substantial portion of the analyte contained in a large volume of air becomes absorbed in a small volume of liquid extractant that can be injected directly into an analytic instrument, such as a liquid chromatograph. As compared with other methods, the direct absorption of an analyte from an arbitrarily large volume of air into a small volume of liquid extractant offers the advantages of low-temperature operation, simplicity, speed and flexibility. While that device has proved effective for detecting hazardous analytes, such as highly carcinogenic primary aromatic amines, at ppb concentrations, it is not suitable for detecting vapors at sub-ppt levels.

SUMMARY OF THE INVENTION

It is a general object of the present invention to provide an improved analytic system which avoids the disadvantages of prior systems, while affording additional structural and operating advantages.

An important feature of the invention is the provision of an analytic system that is portable, and is yet capable of efficiently analyzing trace concentrations of selected vapors in air, at sub-ppt levels.

In connection with the foregoing feature, another feature of the invention is the provision of a system of the type set forth with a sufficiently high air flow rate to permit the sampling of a large volume of air in a fairly short period of time.

It is another feature of the invention to provide a system of the type set forth, which effectively prevents significant losses by adsorption onto solid surfaces.

Yet another feature of the invention is the provision of a system of the type set forth which is of relatively simple and economical construction.

Another feature of the invention is the provision of a preconcentrating apparatus for use in an analytical system of the type set forth.

Still another feature of the invention is the provision of a preconcentration method for use in the analytical system of the type set forth.

These and other features of the invention are attained by providing apparatus for preconcentrating traces of an analyte in a gaseous medium comprising: an elongated gas impermeable container, wettable material disposed in the container and extending substantially the entire length thereof, means for continuously wetting the wettable material adjacent to one end thereof with an analyte-sorbing liquid so that the liquid moves slowly to the other end of the wettable material for wetting substantially the entire length thereof, means for flowing the gaseous medium through the container in contact with the wetted material for trapping and preconcentrating traces of analyte in the sorbing material, and means for removing from the container liquid sorbing material containing the preconcentrated traces of analyte.

Additional objects, advantages and novel features of the invention will be set forth in part in the description which follows, and in part will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention there are illustrated in the accompanying drawings preferred embodiments thereof, from an inspection of which, when considered in connection with the following description, the invention, its construction and operation, and many of its advantages should be readily understood and appreciated.

DESCRIPTION OF THE PREFERRED EMBODIMENTS

Figure 1:
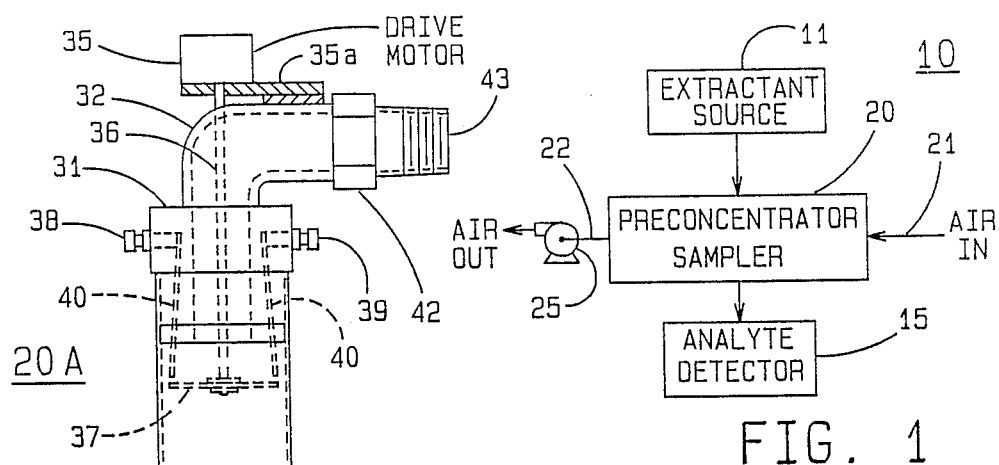
FIG. 1 is a functional block diagram illustrating an analytical system constructed in accordance with and embodying the features of the present invention.

Referring to FIG. 1, there is illustrated an analytical system, generally designated by the numeral 10, which includes an analyte detector 15, which could be an ion mobility spectrometer or other mass spectrometer or other appropriate analytical device. A suitable liquid extractant, i.e., an analyte-sorbing liquid, is fed from an extractant source 11 to a preconcentrator sampler 20, constructed in accordance with and embodying the features of the present invention. Sampled air is fed into the preconcentrator sampler 20 via an inlet port 21, and exits the preconcentrator sampler 20 via an outlet port 22, which is in turn coupled to a suitable air pump 25 for drawing air through the preconcentrator sampler 20. The analyte of interest in the air sample is absorbed by the analyte-sorbing liquid in the preconcentrator sampler 20, and then the liquid sorbing material containing preconcentrated traces of the analyte may be injected directly into the analyte detector 15.

Figures 2, 3, 4:
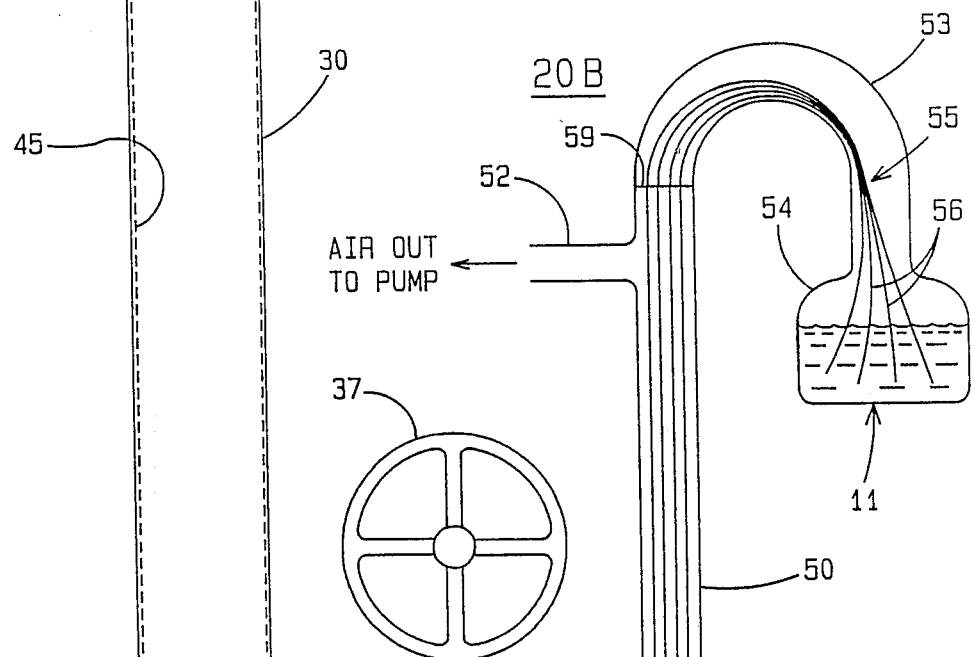
FIG. 2 is a side elevational view of a preconcentrator sampler for use in the system of FIG. 1.
FIG. 3 is an enlarged, bottom plan view of the distributor wheel of the preconcentrator sampler of FIG. 2.
FIG. 4 is a side elevational view of another embodiment of preconcentrator sampler for use in the system of FIG. 1.

Referring now to FIGS. 2 and 3, there is illustrated a first embodiment 20A of the preconcentrator sampler 20 for use in the analytical system 10. The preconcentrator sampler 20A includes an elongated tubular container 30, which is preferably circularly cylindrical in shape with its longitudinal axis disposed substantially vertically, and is formed of a suitable gas-impermeable material. Coupled to the container 30 at its upper end is a cylindrical coupling ring 31. Coupled to the coupling ring 31 is an elbow tube 32, one leg of which extends downwardly through the coupling ring 31 and into the upper end of the tubular container 30, coaxially therewith, and the other leg of which projects laterally outwardly therefrom substantially normal thereto. The coupling ring 31 provides a substantially air-tight coupling between the tubular container 30 and the outer surface of the elbow tube 32. The lower end of the container 30 is closed with an end cap 33 provided with an outlet port 34.

A drive motor 35 is mounted on a suitable support 35a on top of the elbow tube 32, the motor 35 having an output shaft 36 which extends through a complementary opening into the elbow tube 32 and downwardly through the vertical leg thereof, substantially coaxially therewith, being coupled at its lower end to the hub of a distributor wheel 37, which has a spoked configuration and an outer circumference slightly less than the inner circumference of the tubular container 30. Formed at diametrically spaced-apart locations in the coupling ring 31 are two liquid extractant entry ports 38 and 39, respectively communicating at their inner ends with two depending drip tubes 40, the lower ends of which respectively terminate a slight distance above the outer peripheral portion of the distributor wheel 37.

Formed in the side wall of the tubular container 30 adjacent to the lower end thereof is an air inlet hole 41, which is preferably cut at a sharp angle to the wall of the container 30, so as to impart a tangential component, and hence turbulence, to the motion of the inrushing air. Coupled to the outer end of the elbow tube 32 is a fitting 42 which defines an air outlet port 43. It will be appreciated that, in use, the fitting 42 is adapted for coupling to the air pump 25 in FIG. 1 or to a conduit leading thereto. Covering the inner surface of the tubular container 30, from a level above the distributor wheel 37 to a level spaced a slight distance from the end cap 33 is a lining 45 of suitable wettable material. The lining 45 extends around the entire circumference of the inner surface of the tubular container 30, except that it has a suitable opening therein aligned with the air inlet hole 41. Alternatively, the tubular container 30 may be made of a wettable material, such as glass, in which case the lining 45 becomes unnecessary. The term "wettable" as used herein, describes a material, on the surface of which a liquid will form a continuous liquid film, as opposed to beading up. For example, most plastics are not wettable because liquids tend to bead up on the surface thereof. Clean glass, on the other hand, can be wetted by certain liquids, such as aqueous solutions.

In operation, the air to be sampled is pulled into the tubular container 30 through the air inlet port 41 and flows upwardly through the tubular container 30 and out through the elbow tube 32 to the associated pump 25. The fact that the air stream enters and leaves the tubular container 30 in directions substantially normal to the longitudinal axis thereof, together with the relatively high velocity of the air flow, contributes to a turbulent flow of the air through the tubular container 30. Analyte-sorbing liquid is fed by gravity or by a metering pump (not shown) from the extractant source 11 through the inlet ports 38 and 39, and thence flows down through the drip tubes 40 onto the distributor wheel 37. The distributor wheel 37 is rotated by the drive motor 35 so that, as the liquid extractant is dripped thereonto, the extractant is thrown outwardly by centrifugal force onto the inner surface of the lining 45, adjacent to the upper end thereof. The liquid extractant then slowly moves down the wettable surface, aided by gravitational forces, along the length of the lining 45 while wetting substantially the entire surface thereof. As the air sample flows upwardly through the tubular container 30 it contacts the wetted lining 45, and the analyte in the air is selectively absorbed by the analyte-sorbing liquid, and thereby preconcentrated. The analyte-enriched sorbing liquid then flows from the tubular container 30 through the outlet port 34, from which it may be injected into the analyte detector 15.

The analyte-sorbing liquid will vary depending upon the analyte of interest, but it must have a sufficient affinity for the analyte to preferentially absorb most of the vapor phase. For example, acidic and basic extractants will absorb basic and acidic compounds, respectively. Aromatic and aliphatic compounds will tend to be absorbed by aromatic and aliphatic extractants, respectively, especially if the extractant and the absorbed vapor have affinity in their molecular structures. The liquid extractant must also be compatible with the analytical instrument into which the sample is to be injected. Finally, it must be sufficiently stable under the necessary sampling conditions.

To maximize preconcentration of the analyte, it is desirable to minimize the volume of sorbing liquid collected at the outlet port 34. This minimization can be achieved by adding a volatile solute to the analyte-sorbing liquid in the source 11. Then, as the sorbing liquid flows through the preconcentrator sampler 20A, most of the volatile solute will be evaporated by the flowing air, so that the volume of liquid collected at the outlet port 34 will be less than that which was introduced from the source 11. For example, if the liquid extractant comprises an aqueous solution containing about 60-80% methanol, the volume of collected liquid may be reduced by a factor of about 3 to 6.

In a constructional model of the preconcentrator sampler 20A, the tubular container 30 has a length of about 24 inches and an inner diameter of about 2.5 inches. Air is pumped through the tubular container 30 at a rate of about 0.7 cubic meters per minute, in a swirling, highly turbulent motion, which assures rapid transfer of trace analytes to the liquid film which covers the liner 45. The liquid is drained from the bottom of the tubular container 30 at a rate of about 0.7 ml per minute. The lining 45 is formed of Mylar and has a thickness of about 0.10 inches. The distributor wheel 37 is formed of Mylar and the drip tubes 40 have an outer diameter of about 1/16 inch.

Referring to FIG. 4, there is another embodiment 20B of preconcentrator sampler for use in the analytical system 10. The preconcentrator sampler 20B includes an elongated tubular container 50, which is preferably circularly cylindrical in transverse cross section and is preferably oriented with its longitudinal axis disposed substantially vertically. The container 50 is provided with a air inlet port in the side wall thereof adjacent to its lower end, and with an air outlet port 52 in the side wall thereof adjacent to its upper end. It will be appreciated that the air outlet port 52 is adapted to be coupled to the associated air pump 25. Integral with the tubular container 50 at its upper end and communicating therewith is an elbow tube 53 which is generally semi-toroidal in shape, and has a distal end which communicates with an enlarged reservoir 54 which is filled with analyte-sorbing liquid so as to form the extractant source 11. There is also provided an elongated wick 55 which comprises a plurality of wick fibers 56. The wick extends the entire length of the tubular container 50 and through the elbow tube 53, having one end thereof immersed in the analyte-sorbing liquid in the reservoir 54. The other end of the wick 55 is disposed in a necked-down collection portion 57 at the lower end of the tubular container 50 which is, in turn, provided with a valve 58. The fibers 56 of the wick 55 are held apart in the tubular container 50 by fiber separators 59, which are respectively disposed adjacent to the upper and lower ends of the tubular container 50. The valve 58 may be coupled to the analyte detector 15.

In operation, the analyte-sorbing liquid moves slowly by wicking action from the reservoir 54 up along the wick 55 through the elbow tube 53 and thence downwardly through the tubular container 50, being aided in the latter portion of its path by gravity. The air sample containing traces of the analyte of interest is pumped through the tubular container 50 at a relatively high velocity, passing therethrough in a turbulent flow by reason of the high air velocity and the fact that the air inlet 51 and the air outlet 52 are disposed laterally of the tubular container 50. The traces of analyte contained in the sample gas are absorbed by the liquid sorbing material in the wick fibers 56. The analyte-enriched analyte-sorbing liquid is collected in the collector portion 57 and the valve 58 may then be opened to inject the liquid into the analyte detector 15. While only a few of the wick fibers 56 have been illustrated, for simplicity, there may typically be at least one hundred such fibers in the wick 55.

In of the preconcentrator sampler 20B, the liquid extractant continually flows along the wick 55 at a preferably slow rate, e.g., at the rate of about 0.1 ml per minute. The rate of extractant flow along the fiber surfaces is determined partly by the viscosity of the extractant and the wicking properties (interfacial tension and geometry of the fibers), and partly by the siphoning force, i.e. the difference between the heights of the reservoir 54 and the collector portion 57. Alternatively, an osmotic driving force for extractant transport could be engendered by having a much higher salt concentration at the collector portion 57 than at the reservoir 54.

In both of the disclosed embodiments of the preconcentrator sampler 20, to assure that most of the analyte molecules are picked up by the extractant rather than being adsorbed at solid surfaces, the total wetted surface area that is exposed to the sampled air should be several times greater than that of any dry surfaces of the inner wall of the tubular container that may be exposed to the sampled air. For instance, in the preconcentrator sampler 20B, if the inner wall of the tubular container 50 is about 5 cm in diameter, and its length between the air inlet 51 and the air outlet 52 is about 10 cm, yielding a surface area of about 150 cm$^2$, then the total surface area of the wetted fibers 56 should be at least 500 cm$^2$ and preferably about 1000 cm$^2$. This could be satisfied by about one hundred fibers of 2 mm outer diameter or one thousand fibers of 0.2 mm outer diameter. In the preconcentrator sampler 20A the liner 45 substantially completely covers the inner surface of the container 30.

From the foregoing, it can be seen that there has been provided a simple and fast-acting liquid-absorption air sampler for preconcentrating vapors of explosives and other illegal or hazardous substances, which is uniquely adaptable for portable instruments for rapid on-site detection and quantification of such vapors, at sub-ppt levels.

The embodiments of the invention in which an exclusive property or privilege is claimed are defined as follows:

1. A method for preconcentrating traces of an analyte in a gaseous medium, said method comprising the steps of: immersing one end of a wicking material into a reservoir of an analyte-sorbing liquid so that the liquid moves slowly to the other end of the wicking material for wetting most of the length thereof, flowing the gaseous medium over the wetted length of said material in contact therewith for trapping and preconcentrating traces of analyte in the sorbing liquid, and collecting from the other end of the wicking material the sorbing liquid containing the preconcentrated traces of analyte.

2. The method of claim 1, wherein the wettable material is in the form of a hollow cylindrical tube, the wetting step comprising centrifugally discharging the analyte-sorbing liquid onto the inner surface of the tube.

3. The method of claim 1, wherein the movement of the analyte-sorbing liquid to the other end of the wettable material is effected by an osmotic gradient.

4. A method for preconcentrating traces of an analyte in a gaseous medium, said method comprising the steps of: providing a gas impermeable container having an inner wall, providing a length of wettable material disposed on the inner wall with an analyte-sorbing liquid so that the liquid moves slowly to the other end of the wettable material for wetting most of the length thereof, flowing the gaseous medium over the wetted length of said material in contact therewith for trapping and preconcentrating traces of analyte in the sorbing liquid, assuring that the total wetted surface area of the wettable material exposed to the gaseous medium is substantially greater than any dry surfaces of the inner wall of the container exposed to the gaseous medium, and collecting from the other end of the wettable material the sorbing liquid containing the preconcentrated traces of analyte.

5. The method of claim 4, wherein said one end of the wettable material is disposed above said other end thereof so that movement of the analyte-sorbing liquid from said one end to said other end is effected by gravity.

6. The method of claim 4 wherein the flowing step includes imparting turbulence to the gaseous medium.

7. The method of claim 4, wherein the sorbing liquid includes a volatile solute.

8. Apparatus for preconcentrating traces of an analyte in a gaseous medium comprising: an elongated gas impermeable container, wettable material disposed in said container and extending through most of the length thereof, means for continuously wetting said wettable material adjacent to one end thereof with an analyte-sorbing liquid so that the liquid moves slowly to the other end of said material for wetting most of the length thereof, means for flowing the gaseous medium through said container in contact with said wetted material for trapping and preconcentrating traces of analyte in the sorbing liquid, means for removing from said container the sorbing liquid containing the preconcentrated traces of analyte, and a reservoir of the analyte-sorbing liquid, in communication with a tube integral with the container, said wettable material being a wicking material, and one end of said wicking material being immersed in the liquid in said reservoir.

9. The apparatus of claim 8, wherein said wicking material has a total surface area substantially greater than that of the inner surface of said container exposed to the gaseous medium.

10. The apparatus of claim 8, wherein said wicking material comprises a bundle of wicking fibers.

11. The apparatus of claim 8, and further comprising analyte detection means adjacent to the liquid removing means in which the removed sorbing liquid is injected, said analyte detection means responsive to analyte traces in the removed sorbing liquid for producing an output signal.

12. Apparatus for preconcentrating traces of an analyte in a gaseous medium comprising: an elongated gas impermeable container having an inner wall, wettable material disposed on the inner wall of the container and extending through most of the length thereof, means for continuously wetting said wettable material adjacent to one end thereof with an analyte-sorbing liquid so that the liquid moves slowly to the other end of said material for wetting most of the length thereof, means for flowing the gaseous medium through said container in contact with said wetted material for trapping and preconcentrating traces of analyte in the sorbing liquid, and means for removing from said container the sorbing liquid containing the preconcentrated traces of analyte, wherein any dry surfaces of the inner wall of the container onto which the analyte could adsorb before coming in contact with the liquid are negligibly small.

13. The apparatus of claim 12, wherein said container has a longitudinal axis which is disposed substantially vertically, said one end of said wettable material being disposed at the upper end of said container, whereby movement of the analyte-sorbing liquid toward the other end of said wettable material is effected by gravity.

14. The apparatus of claim 12, wherein said container has gas input ports respectively disposed adjacent to the opposite ends thereof and arranged for introducing the gaseous medium to said container and removing the gaseous medium from said container in directions laterally thereof, said means for flowing the gaseous medium through said container including pump means coupled to the outlet port.

15. The apparatus of claim 12 and further comprising a means for inducing turbulence to the gaseous medium within the container.

16. Apparatus for preconcentrating traces of an analyte in a gaseous medium comprising: an elongated gas impermeable container having an inner surface, wettable material disposed along said inner surface of said container for most of the length thereof, means for introducing an analyte-sorbing liquid into said container near one end thereof, distributing means disposed near said one end of said container for receiving the analyte-sorbing liquid and for delivering it laterally onto said wettable material near one end thereof around the perimeter thereof so that the liquid moves slowly to the other end of said wettable material for wetting most of the length thereof, means for flowing the gaseous medium through an inlet opening into said container, the gaseous medium in contact with said wetted material for trapping and preconcentrating traces of analyte in the sorbing liquid, and means for removing from said container the sorbing liquid containing the preconcentrated traces of analyte, wherein any solid surfaces onto which the analyte could adsorb before coming in contact with the liquid are negligibly small.

17. The apparatus of claim 16, wherein said container is substantially in the form of a cylindrical tube.

18. The apparatus of claim 17, wherein the distributing means includes rotating means for discharging the analyte-sorbing liquid by dispersing it radially outward onto the wettable material by centrifugal force.

19. The apparatus of claim 18, wherein said distributing means includes a circular ring disposed within said container coaxially therewith, a drive means for rotating said ring, and liquid inlet means for delivering analyte-sorbing liquid onto said ring.

20. The apparatus of claim 19, wherein said inlet means includes a drip tube having an exit end disposed immediately above said ring for dripping the analyte-sorbing liquid onto said ring.

21. The apparatus of claim 16, wherein the wettable material is glass and the liquid is an aqueous solution.

22. The apparatus of claim 16, wherein said wettable material covers most of the inner surface of said container.

* * * * *

UNITED STATES PATENT AND TRADEMARK OFFICE
CERTIFICATE OF CORRECTION

PATENT NO. : 4,977,095
DATED      : December 11, 1990
INVENTOR(S): Solomon Zaromb It is certified that error appears in the above-identified patent and that said Letters Patent is hereby corrected as shown below:

Title page:
Item (19) change "Zaromb" to Zaromb et al.

Item (75) Inventor:, change "Inventor" to --Inventors--, and add --William Prepejchal-- as a joint inventor.

Signed and Sealed this

Twenty-first Day of July, 1992

Attest:

DOUGLAS B. COMER

*Attesting Officer*        *Acting Commissioner of Patents and Trademarks*